United States Patent [19]

Ashbee

[11] 4,257,265
[45] Mar. 24, 1981

[54] SELF-STRESSED MODE 1 FRACTURE MECHANICS TEST PIECE

[75] Inventor: Kenneth H. G. Ashbee, Bristol, England

[73] Assignee: The United States of America as represented by the Secretary of the Air Force, Washington, D.C.

[21] Appl. No.: 76,720

[22] Filed: Sep. 19, 1979

[51] Int. Cl.³ .............................................. G01N 3/08
[52] U.S. Cl. ................................. 73/150 A; 73/785; 73/799
[58] Field of Search ................. 73/760, 827, 834, 785, 73/849, 850, 821, 799, 150 A; 29/407

[56] References Cited

U.S. PATENT DOCUMENTS

| 3,151,480 | 10/1964 | Schultz | 73/141 |
| 3,572,091 | 3/1971 | McFarland . | |
| 3,649,127 | 3/1972 | Kersch et al. | 356/109 |
| 3,842,664 | 10/1974 | Conway, Jr. . | |
| 3,979,949 | 9/1976 | Smith . | |
| 4,107,980 | 8/1978 | Crane et al. . | |

Primary Examiner—Jerry W. Myracle
Attorney, Agent, or Firm—Donald J. Singer; Arsen Tashjian

[57] ABSTRACT

Two radial cuts are made in a disc-shaped solid, the wedge (or sector) thereby produced is removed, and the exposed faces of the radial cuts are forced into contact with each other. By bonding (or welding) together the faces of the radial cuts, a self-stressed disc, capable of propagating a pure mode 1 crack, is created.

7 Claims, 4 Drawing Figures

U.S. Patent  Mar. 24, 1981  4,257,265

SELF-STRESSED MODE 1 FRACTURE MECHANICS TEST PIECE

STATEMENT OF GOVERNMENT INTEREST

The invention described herein may be manufactured and used by or for the Government for governmental purposes without the payment of any royalty thereon.

BACKGROUND OF THE INVENTION

This invention relates generally to a test piece (i.e., a test specimen) and, more particularly, to a method of manufacturing a self-stressed (mode 1) fracture mechanics test piece, and also to the novel structure of the test piece itself.

An urgent need arose in the art for the results of a fracture mechanics test in order to evaluate a concept; and, as a result of that need, the manufacture of a plurality of identical test pieces became necessary.

My inventive fracture mechanics test piece, and the method of manufacturing that test piece, are the outgrowth of that necessity, and constitute a significant advance in the state-of-the-art.

SUMMARY OF THE INVENTION

My invention teaches a method of manufacturing a reproducible self-stressed, fracture mechanics test piece, and also teaches the structure of the test piece itself.

Accordingly, the principal objects of this invention are to provide a structurally novel test piece and to permit the manufacture of it and copies thereof.

These principal objects, as well as other related objects, of this invention will become readily apparent after a consideration of the description of my invention, coupled with reference to the Figures of the drawings.

DESCRIPTION OF THE INVENTIVE METHOD

With reference to FIGS. 1—4, inclusive, the very basic and fundamental steps of my inventive method of manufacturing a reproducible self-stressed, (mode 1) fracture mechanics test piece comprises, essentially, six steps.

Firstly, I fabricate a metal disc having a center and a radius of preselected length. I use a 16 gauge (i.e., 0.064 inch thick) aluminum sheet; and, with a punch and die operation, I fabricate from the sheet a disc (such as 20, FIGS. 1-4, inclusive) having a diameter (such as "D", FIG. 4) of 3 inches (i.e., a radius of 1½ inches).

Next, I make a centrally-located opening (such as 21, FIGS. 1-4, inclusive) in the metal disc 20. By employing a punch and die operation, I make a ½ inch diameter central hole 21.

Figure 1:
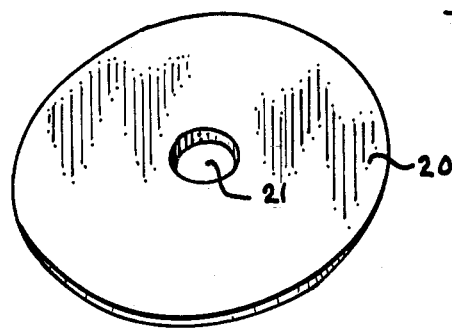
FIGS. 1, 2 and 3 are perspective views, in simplified form, which collectively constitute a pictorial representation of the result of the performance of the various steps of my inventive method and, or course, of the inventive reproducible test piece that is thereby produced.
Figure 2:
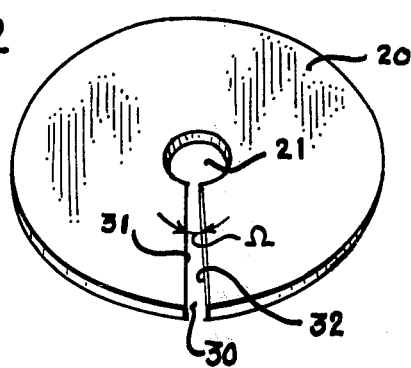
Figure 3:
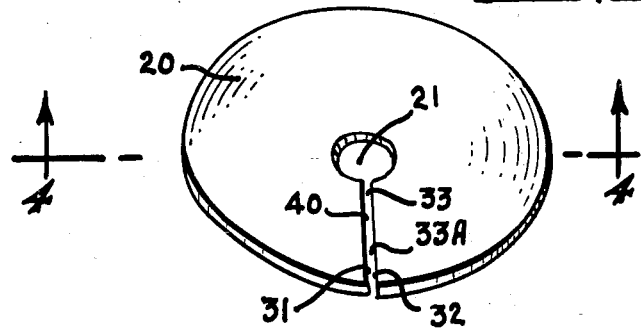

Then, I cut, and remove, a sector portion (not shown) from the metal disc 20, which results in a sector-shaped space (such as 30, FIG. 2) being formed and defined by two adjacent radial edges (such as 31 and 32, FIGS. 2 and 3). I use a 0.006 inch milling cutter to cut and remove the sector; and, a 0.012 inch cut at the surface of the central hole 21 produces a sector space 30 having a sector angle (such as $\Omega$, FIG. 2) of 2 degrees and 50 minutes (i.e., 0.05 rads).

Next, I shape the metal disc 20 (from which the sector, or wedge portion, has been removed), essentially into the form of a female cone (i.e., a truncated and inverted cone) having a gap (such as 33, FIG. 3) between the two radial edges 31 and 33, with the gap 33 being smaller than the sector-shaped space 30 (or the removed sector portion). As a matter of preference, I shape the metal disc 20 by pressing.

Then, I insert a preselected adhesive, (such as 40, FIG. 3) having a known critical strain energy release rate, in the gap 33 between the two radial edges 31 and 32, with the result that a glue line (such as 33A, FIG. 3) is formed.

Next, I close the gap 33 containing the adhesive 40 by squeezing (preferably with a vise) the metal disc 20 across a chord perpendicular to the glue line 33A and, simultaneously, by gripping the two radial edges 31 and 32 (preferably with a toolmaker's clamp) until the adhesive 40 is cured and the edges 31 and 32 are thereby joined by bonding.

Lastly, I constrain the bonded female cone to be flat, thereby causing it to be self-stressed. As a matter of preference, I constrain the cone by clamping it between ½ inch thick slabs, one of plate glass in order that the crack length may be seen, and the other of mild steel.

It is here to be noted that, as a matter of preference, my inventive method includes the additional step of cleaning, and anodizing (with a phosphoric acid anodizing solution), the aluminum metal disc 20. This additional step may be performed at any time prior to the step of inserting a preselective adhesive 40 in the gap 33 between the two radial edges 31 and 32 of the female cone (not shown).

DESCRIPTION OF THE PREFERRED EMBODIMENT OF THE TEST PIECE

Figure 4:
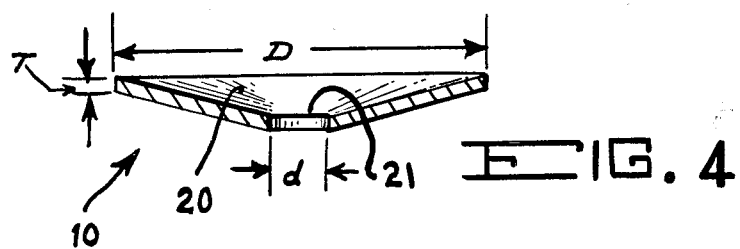
FIG. 4 is a side elevation view, in simplified pictorial form and in cross section, of the preferred embodiment of the resultant test piece, as shown in FIG. 3, and as viewed along line 4—4 of FIG. 3.

With reference to FIGS. 3 and 4, therein is shown, in different views, the preferred embodiment 10 of my inventive self-stressed (mode 1) fracture mechanics test piece.

As can be easily seen, it comprises a metal disc 20 having: a centrally located opening 21; a sector-shaped space (such as 30, FIG. 2) that is defined, in part, by a first radial edge 31 and an adjacent second radial edge 32, and that has been closed to form a gap 33 (which, of course, is smaller than the pre-existing sector-shaped space 30, FIG. 2); and, a preselected adhesive, generally designated 40, having a known critical energy release rate, that is interposed between and joins the radial edges 31 and 33.

As a matter of preference and not of limitation, the metal disc 20 is made of cleaned and anodized aluminum.

For a specific purpose, as set out hereinbefore, the test piece has a diameter "D" of 3 inches and a thickness "T" of 0.064 inches; the centrally-located opening 21 is in the form of a circle having a diameter of "d" of ½ inch; and the sector-shaped space 30, FIG. 2, has a sector angle of 2 degrees and 50 minutes.

PHENOMENON INVOLVED IN MAKING AND IN USING THE TEST PIECE

It can be shown, with reference to the test piece 10, FIGS. 3 and 4, that there exist simple relationships between the stress intensity factor, the crack formation energy, and the strain energy release on one hand, and the crack length on the other hand.

In that regard, I hereby offer to make proof of the above-stated concept by rigorous mathematical analysis. Said analysis is not presented here in the interest of maintaining simplicity of this application, consistent with the extent of patent coverage that I seek.

CONCLUSION

It is abundantly clear from all of the foregoing, and from the Figures of the drawings, that the stated principal objects, as well as related objects, of my invention have been achieved.

Additionally, while there have been shown and described the unique and fundamental steps of my basic inventive method, the variation thereof, and the preferred structural embodiment 10, FIGS. 3 and 4, of my inventive test piece, it is to be understood that other variations of my basic inventive method, and other embodiments of my inventive test piece, will occur to, and can be made by, those of ordinary skill in the art, without departing from the spirit of my invention as a whole. For example: (a) the disc 20 may be made of stainless steel; (b) the radial edges 31 and 32 may, in appropriate circumstances, be joined by any suitable means, such as by welding; and (c) the metal test piece 20 may be cleaned and anodized by a procedure which includes the use of a chromic acid solution.

What is claimed is:

1. A method of manufacturing a self-stressed fracture mechanics test-piece, comprising the steps of:
    a. fabricating a metal disc having a center and a radius of preselected length;
    b. making a centrally-located opening in said metal disc;
    c. cutting, and removing, a sector portion from said metal disc, whereby a sector-shaped space defined by two adjacent radial edges is formed;
    d. shaping said metal disc, from which said sector portion has been removed, essentially into the form of a female cone having a gap between said two radial edges, with said gap being smaller than said sector-shaped space;
    e. inserting a preselected adhesive, having a known critical strain energy release rate, in said gap between said two radial edges, whereby a glue line is formed;
    f. closing said gap containing said adhesive by squeezing said metal disc across a chord perpendicular to said glue line and, simultaneously, by gripping said two radial edges until said adhesive is cured and said edges are thereby joined by bonding;
    g. and, constraining said bonded female cone to be flat, thereby causing it be self-stressed.
2. A method, as set forth in claim 1, wherein:
    a. said metal disc is made of aluminum;
    b. and, said centrally-located opening in said metal disc is in the form of a circle having a diameter of preselected length.
3. A method, as set forth in claim 2, wherein said method further comprises the additional step of cleaning and anodizing said aluminum metal disc.
4. A method, as set forth in claim 3, wherein said step of cleaning and anodizing said aluminum metal disc includes the use of a phosphoric acid anodizing solution.
5. A fracture mechanics test-piece comprising a self-stressed metal disc having:
    a. a centrally located opening;
    b. a sector-shaped space, defined by a first radial edge and an adjacent second radial edge, that is closed to a gap;
    c. and, a preselected adhesive, having a known critical strain energy release rate, disposed within said gap and interposed between, and joining, said radial edges;
    whereby, said test-piece has been transformed from a flat condition to a bonded conical condition, and thereafter has been self-stressed by having been transformed from a bonded conical condition to a flat bonded condition.
6. A fracture mechanics test-piece, as set forth in claim 5, wherein said metal disc is made of cleaned and anodized aluminum.
7. A fracture mechanics test-piece, as set forth in claim 6 wherein:
    a. said metal disc has a diameter of three inches and a thickness of sixtyfour one hundredths of one inch;
    b. said centrally located opening is in the form of a circle having a diameter of one half of one inch;
    c. and, said sector-shaped space has a sector angle of two degrees and fifty minutes.

* * * * *